(12) United States Patent
Shue et al.

(10) Patent No.: US 7,066,906 B2
(45) Date of Patent: Jun. 27, 2006

(54) DISPOSABLE SYRINGE

(76) Inventors: Ming-Jeng Shue, No. 14, Lane 8, Chung-I St., Hsi Dist., Taichung City (TW); Phillip Shue, No. 14, Lane 8, Chung-I St., Hsi Dist., Taichung City (TW)

( * ) Notice: Subject to any disclaimer, the term of this patent is extended or adjusted under 35 U.S.C. 154(b) by 0 days.

(21) Appl. No.: 10/143,461

(22) Filed: May 10, 2002

(65) Prior Publication Data
US 2003/0212367 A1    Nov. 13, 2003

(51) Int. Cl.
*A61M 5/00* (2006.01)
(52) U.S. Cl. .................... 604/110; 604/196
(58) Field of Classification Search ........... 604/110, 604/187, 181, 263, 195, 192, 218
See application file for complete search history.

(56) References Cited

U.S. PATENT DOCUMENTS 6,196,997 B1 *  3/2001  Saito ................ 604/110

* cited by examiner

*Primary Examiner*—Kevin C. Sirmons

(57) ABSTRACT

A disposable syringe has a needle seat with an upper segment adapted to be sleeved over by a needle unit, and a lower segment retained in a passage of a barrel. A plunger has a stem portion movable in the passage, a surrounding engaging portion in sealing contact with the passage so as to be moved by the stem portion of the plunger in a position of use, and a head which is moved towards and is held by a grip segment in the needle seat when the surrounding engaging portion is depressed by an edge portion of the needle seat by virtue of a continuing depression force of the plunger, thereby permitting the needle seat to be brought into the passage for safe disposal.

11 Claims, 10 Drawing Sheets

DISPOSABLE SYRINGE

BACKGROUND OF THE INVENTION

1. Field of the Invention

This invention relates to a disposable syringe, more particularly to a disposable syringe which enables a needle unit to be retracted within a barrel after use for safe disposal and use.

2. Description of the Related Art

Referring to FIG. 1, a conventional disposable syringe assembly 10 is shown to include a barrel 11, a plunger 12 and a needle unit 13. The barrel 11 has an open neck end portion 111 to which a needle hub 131 of the needle unit 13 is attached, and an open rear end from which the plunger 12 is slidably inserted into the barrel 11. A forward end 121 of the plunger 12 is snugly fitted against, but is nevertheless slidable along, the inner surface of the barrel 11 through a distance (L). The needle unit 13 further has a needle 132 extending from the needle hub 131, and a cap 133 with an open end which is fitted around an outer edge of the needle hub 131, with the needle 132 enclosed within the cap 133. The cap 133 is removed from the needle hub 131 when the syringe assembly 10 is to be used, and is sleeved back after use to ensure that the needle 132 is covered. Thereafter, the needle unit 13 is detached from the barrel 11 along with the cap 133 covering the needle 132.

However, the medical or nursing personnel who has to handle the conventional disposable syringe assembly 10 is exposed to the risk of being pricked by the needle 132 when sleeving the cap 133 back on the needle hub 131 after using the disposable syringe assembly 10 since the dimension of the open end of the cap 133 is small. Moreover, as forward movement of the forward end 121 of the plunger 12 terminates at the point (P1), some medicine or blood may remain within the neck end portion 111, which may cause contamination to the personnel who is unfortunately pricked by the needle 132.

SUMMARY OF THE INVENTION

An object of the present invention is to provide a disposable syringe which provides greater safety in use and which eliminates the aforesaid drawback of the prior art.

According to this invention, the disposable syringe includes a barrel having an inner surrounding barrel wall surface which surrounds an axis and which confines a passage. The passage has lower and upper open ends disposed opposite to each other in a longitudinal direction parallel to the axis. The inner surrounding barrel wall surface includes a larger-diameter segment and a smaller-diameter segment which are disposed proximate to the lower and upper open ends, respectively, and which cooperatively form a surrounding shoulder portion therebetween.

A tubular needle seat is insertable into the passage from the lower open end toward the upper open end, and includes a lower surrounding edge portion disposed to abut against the first surrounding shoulder portion, an upper surrounding edge portion disposed opposite to the lower surrounding edge portion in the longitudinal direction, and a surrounding seat wall interposed therebetween. The surrounding seat wall has an inner tubular wall surface which surrounds the axis to confine a duct which forms a grip segment, and an outer tubular wall surface. The outer tubular wall surface includes a lower segment proximate to the lower surrounding edge portion, and an upper segment disposed opposite to the lower segment and proximate to the upper surrounding edge portion. When the upper surrounding edge portion is forced to extend outwardly of the upper open end after the tubular needle seat is inserted into the passage, the lower segment will be brought to a position of use, where the lower segment engages and is retained at the smaller-diameter segment by virtue of a first friction force generated therebetween while the lower surrounding edge portion abuts against the surrounding shoulder portion. In addition, when the upper surrounding edge portion is forced against the first friction force so as to be retracted into the passage via the upper open end, the upper surrounding edge portion will be brought to a retracted position, where the lower segment and the surrounding lower edge portion are remote from the smaller-diameter segment and the first surrounding shoulder portion, respectively. The outer tubular wall surface is adapted to be sleeved over by a needle hub of a needle unit so as to communicate the duct with the needle hub.

A plunger includes a stem portion which is disposed to be movable in the passage and which has inner and outer segments opposite to each other in the longitudinal direction. The outer segment extends outwardly of the lower open end of the passage. An actuated end extends from the outer segment so as to be actuated to move the stem portion along the passage. A surrounding engaging portion is retainingly sleeved on the inner segment by virtue of a second friction force, and is in sealing contact with and is slidable relative to the larger-diameter segment so as to be moved with the stem portion in the position of use. A head extends from the inner segment toward the grip segment. When the surrounding engaging portion is brought by the inner segment to engage the lower surrounding edge portion and is depressed by the lower surrounding edge portion by virtue of a third force generated as a consequence of continuing movement of the inner segment towards the smaller-diameter segment, the third force is greater than the second friction force such that the surrounding engaging portion is retained by the lower surrounding edge portion to thereby permit the head to move towards the grip segment of the tubular needle seat and to be held by virtue of a fourth friction force that is greater than the first friction force.

BRIEF DESCRIPTION OF THE DRAWINGS

Other features and advantages of the present invention will become apparent in the following detailed description of the preferred embodiments of the invention, with reference to the accompanying drawings, in which.

DETAILED DESCRIPTION OF THE PREFERRED EMBODIMENTS

Figure 1:
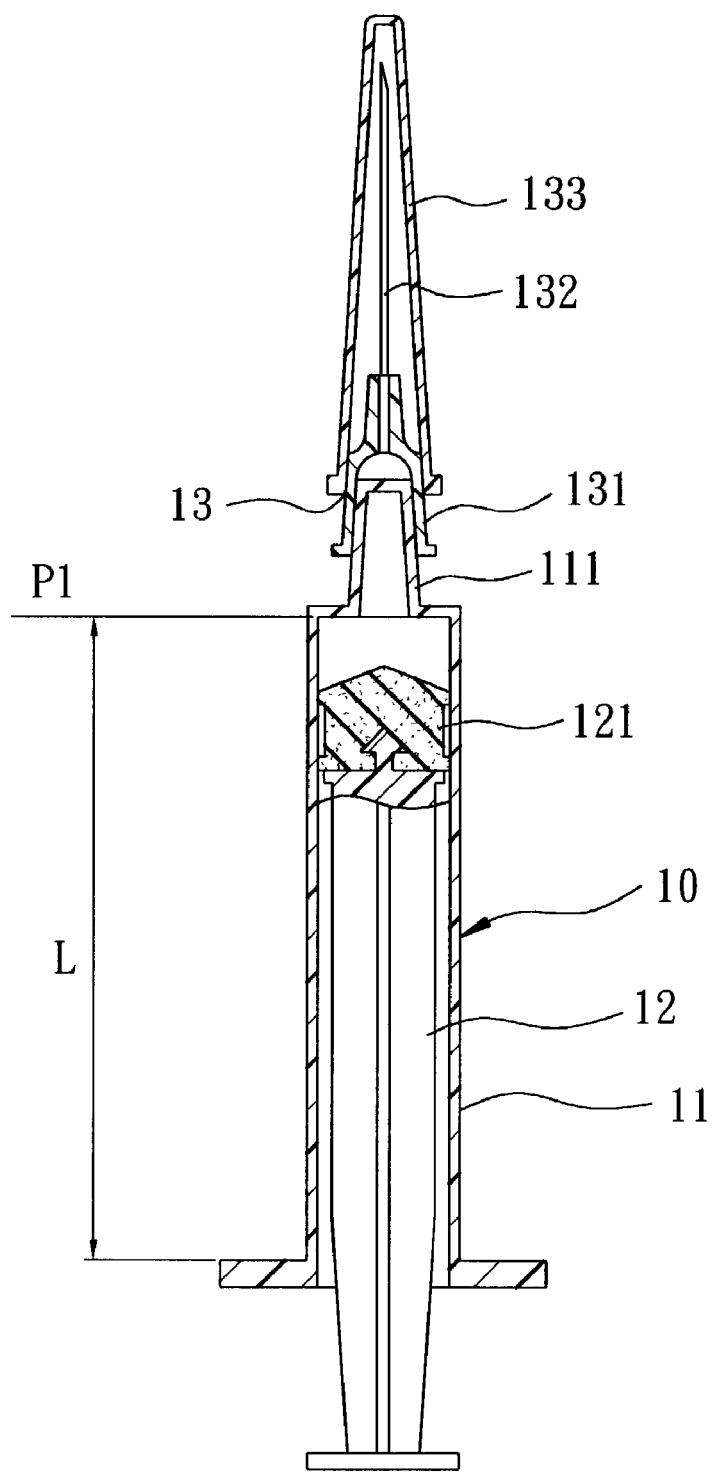
FIG. 1 is a longitudinal cross-sectional view of a conventional disposable syringe assembly.

Before the present invention is described in greater detail, it should be noted that same reference numerals have been used to denote like elements throughout the specification.

Figure 2:
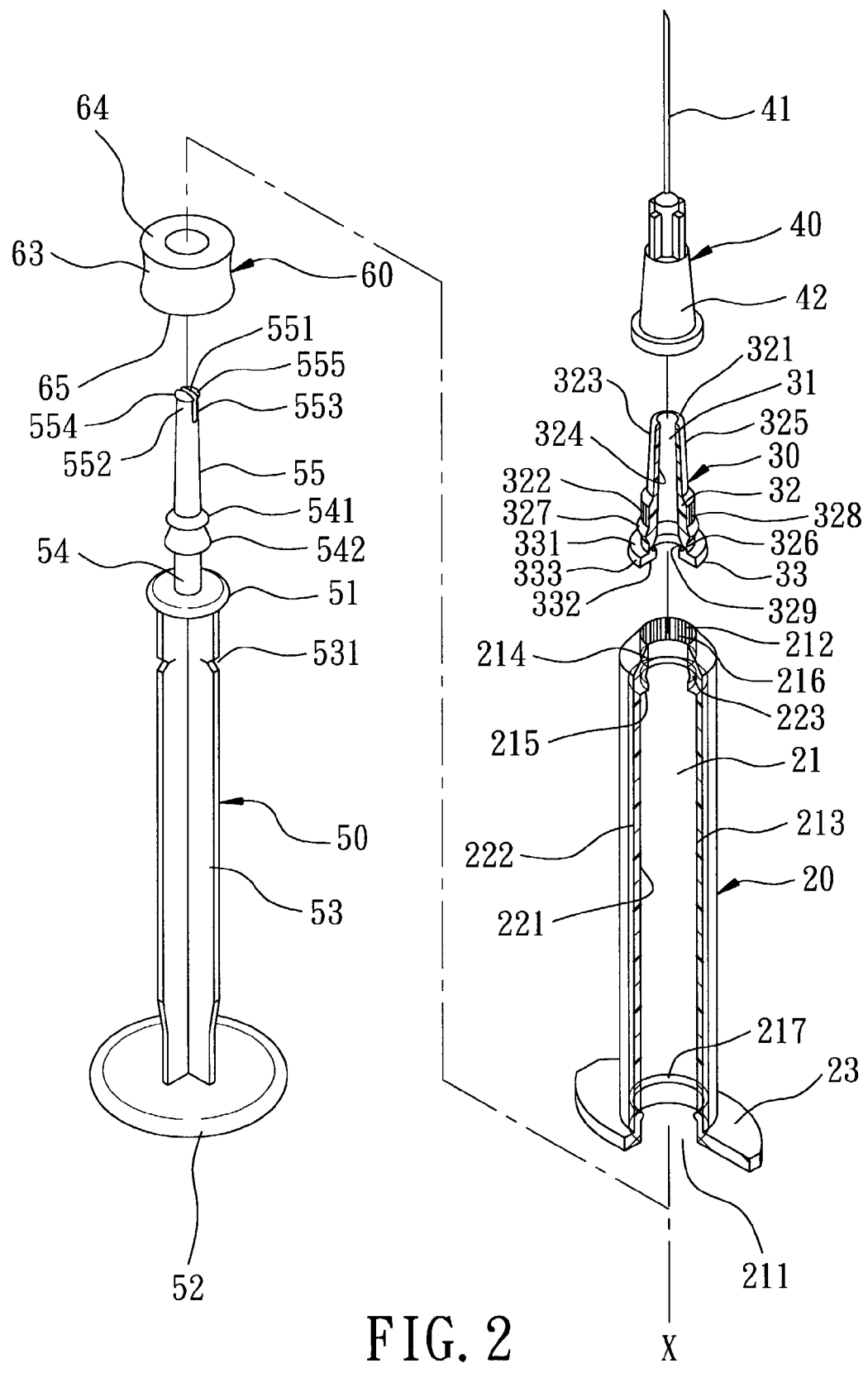
FIG. 2 is an exploded perspective view of a first preferred embodiment of a syringe according to this invention for use with a needle unit to form a syringe assembly.
Figure 3:
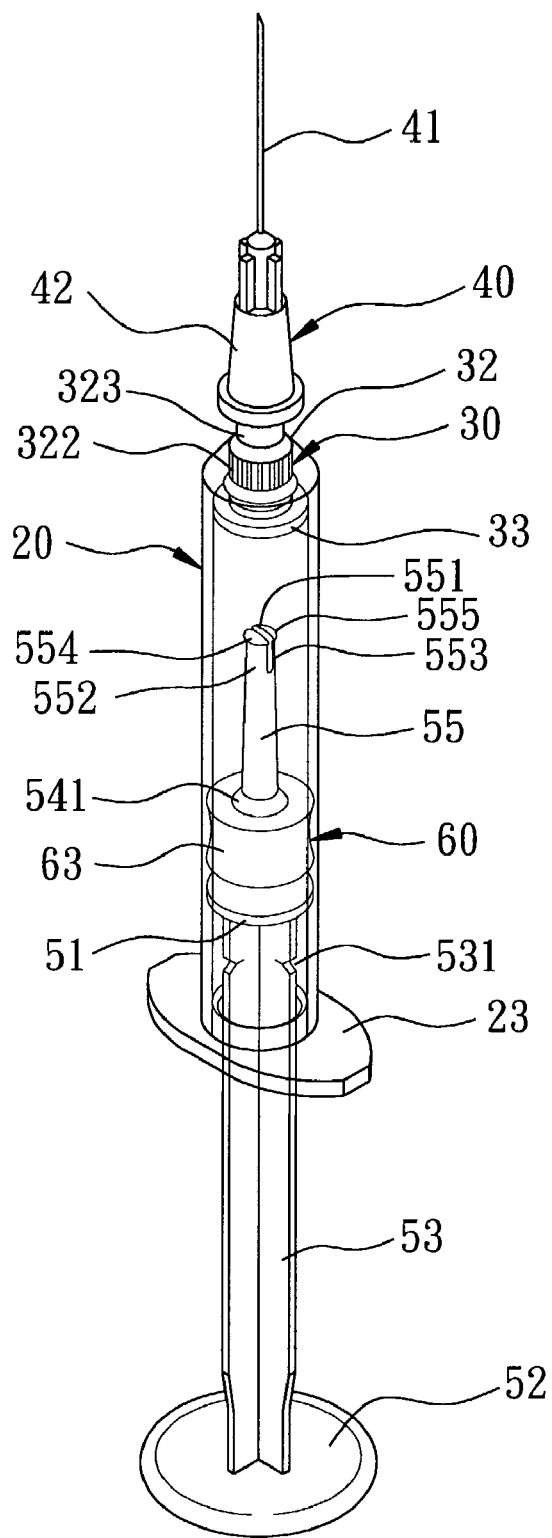
FIG. 3 is a perspective view of the syringe assembly according to the first preferred embodiment.
Figure 4:
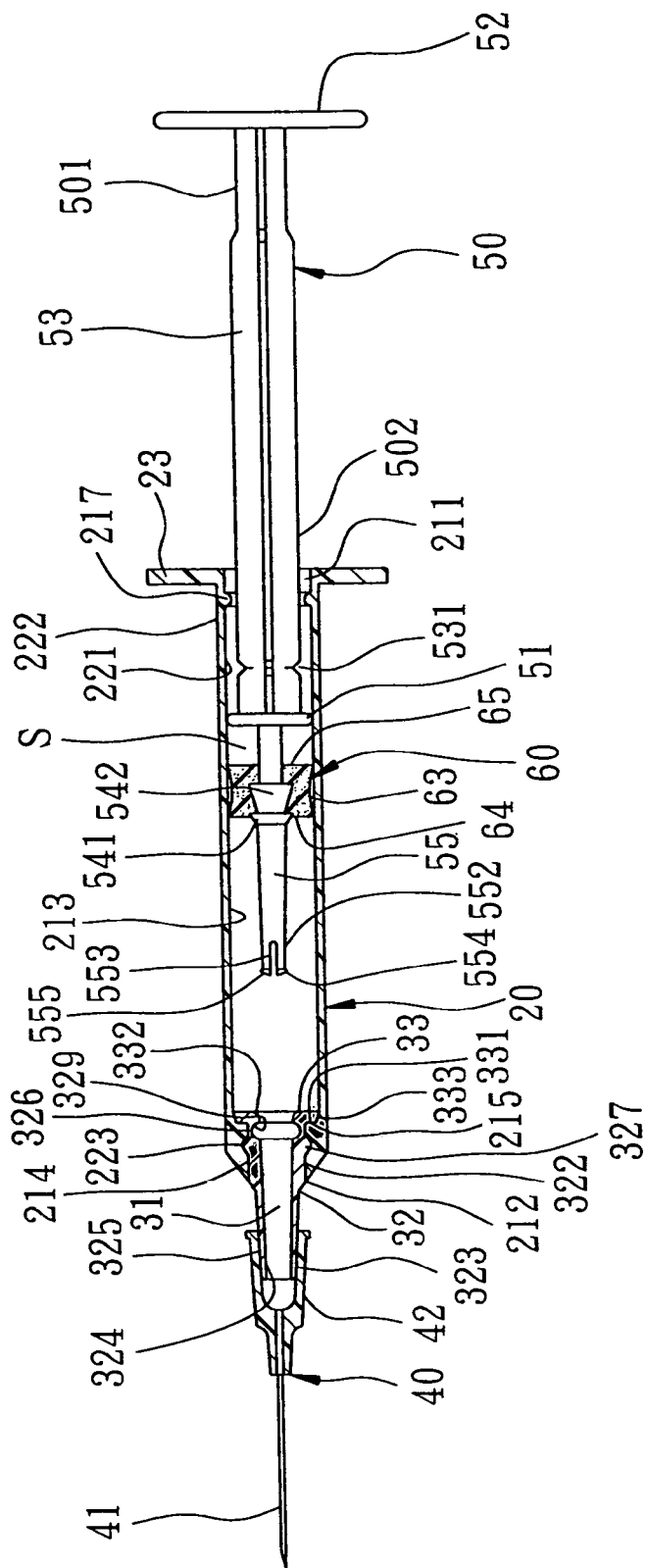
FIG. 4 is a longitudinal cross-sectional view showing the syringe assembly during use.

Referring to FIGS. 2, 3 and 4, the first preferred embodiment of the disposable syringe according to the present invention is shown to be used with a needle unit 40 to form a syringe assembly. The needle unit 40 includes a needle hub 42 and a needle 41 which is securely affixed to the needle hub 42. The syringe in this embodiment is shown to comprise a barrel 20, a tubular needle seat 30, and a plunger 50.

The barrel 20 has an inner surrounding barrel wall surface 221 which surrounds an axis X and which confines a passage 21. The passage 21 has lower and upper open ends 211, 212 which are disposed opposite to each other in a longitudinal direction parallel to the axis X. The inner surrounding barrel wall surface 221 includes a larger-diameter segment 213 and a smaller-diameter segment 214 which are disposed proximate to the lower and upper open ends 211, 212, respectively, and which cooperatively form a first surrounding shoulder portion 215 therebetween. A finger flange 23 is disposed on an outer surrounding barrel wall surface 222 of the barrel 20 at the lower open end 211. The smaller-diameter segment 214 is formed with a retaining groove 223 proximate to the first surrounding shoulder portion 215, and an axially extending friction spline portion 216 remote from the first surrounding shoulder portion 215. A protruding ring 217 is formed on and projects inwardly and radially from the larger-diameter segment 213 adjacent to the lower open end 211.

The tubular needle seat 30 is disposed to be insertable into the passage 21 from the lower open end 211 toward the upper open end 212. The needle seat 30 includes a lower surrounding edge portion 33 disposed to abut against the first surrounding shoulder portion 215 and having an outer surrounding surface 333 which abuts sealingly against the larger-diameter segment 213, an upper surrounding edge portion 321 disposed opposite to the lower surrounding edge portion 33 in the longitudinal direction, and a surrounding seat wall 32 interposed therebetween.

The seat wall 32 has an inner tubular wall surface 324 which surrounds the axis X to confine a duct 31. The duct 31 has a diameter that gradually decreases from the lower surrounding edge portion 33 to the upper surrounding edge portion 321. The inner tubular wall surface 324 forms a grip segment. In this embodiment, the grip segment includes a concave portion 326 which extends inwardly from the inner tubular wall surface 324 in radial directions relative to the axis X to form a second surrounding shoulder portion 329 that is adjacent to the lower surrounding edge portion 33.

The seat wall 32 further has an outer tubular wall surface 325 which includes lower and upper segments 322, 323. The lower segment 322 is proximate to the lower surrounding edge portion 33, and has a retaining protrusion 327 formed thereon. When the upper surrounding edge portion 321 is forced to extend outwardly of the upper open end 212 of the barrel 20 after the tubular needle seat 30 is inserted into the passage 21, the lower segment 322 will be brought to a position of use, as shown in FIG. 4, where the lower segment 322 engages and is retained at the smaller-diameter segment 214 by virtue of a first friction force generated as a result of retaining engagement of the retaining protrusion 327 in the retaining groove 223, while an upper edge surface 331 of the lower surrounding edge portion 33 abuts against the first surrounding shoulder portion 215 of the barrel 20. The lower segment 322 further has an axially extending friction spline portion 328 which cooperates with the friction spline portion 216 of the smaller-diameter segment 214 to form a spline member so as to prevent relative rotation between the needle seat 30 and the barrel 20. The upper segment 323 is disposed opposite to the lower segment 322 and proximate to the upper surrounding edge portion 321, and is adapted to be sleeved over by the needle hub 42 of the needle unit 40 so as to communicate the duct 31 of the needle seat 30 with the needle hub 42.

The plunger 50 includes a stem portion which is movable in the passage 21 of the barrel 20. The stem portion has a plurality of wing plates 53 angularly displaced from one another, a surrounding flange 51 disposed on upper edges of the wing plates 53, a connecting shank 54 extending from the surrounding flange 51, and a retaining protrusion 542. The wing plates 53 are tapered downwardly. On the other hand, the stem portion includes inner and outer segments 502,501 opposite to each other in the longitudinal direction. The outer segment 501 extends outwardly of the lower open end 211 of the barrel 20. An actuated end 52, which is a thumb rest, extends from the outer segment 501 so as to be actuated to move the stem portion along the passage 21.

The plunger 50 further includes a head which has a tapered surrounding abutting portion 541 that extends from the retaining protrusion 542 of the inner segment 502 toward the grip segment of the needle seat 30, and a spindle portion 55 which extends upwardly from the surrounding abutting portion 541 along the axis and which terminates at two split halves 552, 553 that are spaced apart from each other in a direction transverse to the longitudinal direction with a concave space 551 in between. The split halves 552, 553 respectively have upper terminal anchoring edges 554, 555. Preferably, the spindle portion 55 has an outer diameter which decreases from the surrounding abutting portion 541 toward the split halves 552, 553.

A deformable surrounding engaging portion 60, such as made of an elastic material, is retainingly sleeved on the whole retaining protrusion 542 of the inner segment 502 and a portion of the surrounding abutting portion 541 to generate a second friction force. The surrounding engaging portion 60 has upper and lower end faces 64, 65 opposite to each other in the longitudinal direction and proximate to and distal from the lower surrounding edge portion 33 of the needle seat 30, respectively, and an outer surrounding surface 63 disposed therebetween. The lower end face 65 is distal from the surrounding flange 51 by a space (S). The outer surrounding surface 63 sealingly contacts and is slidable relative to the larger-diameter segment 213 of the barrel 20 so as to be moved with the stem portion. Preferably, the outer surrounding surface 63 is concaved toward the axis X to decrease contact area between the outer surrounding surface 63 and the larger-diameter segment 213 so as to facilitate sliding movement of the surrounding engaging portion 60 relative to the larger-diameter segment 213.

Figure 5:
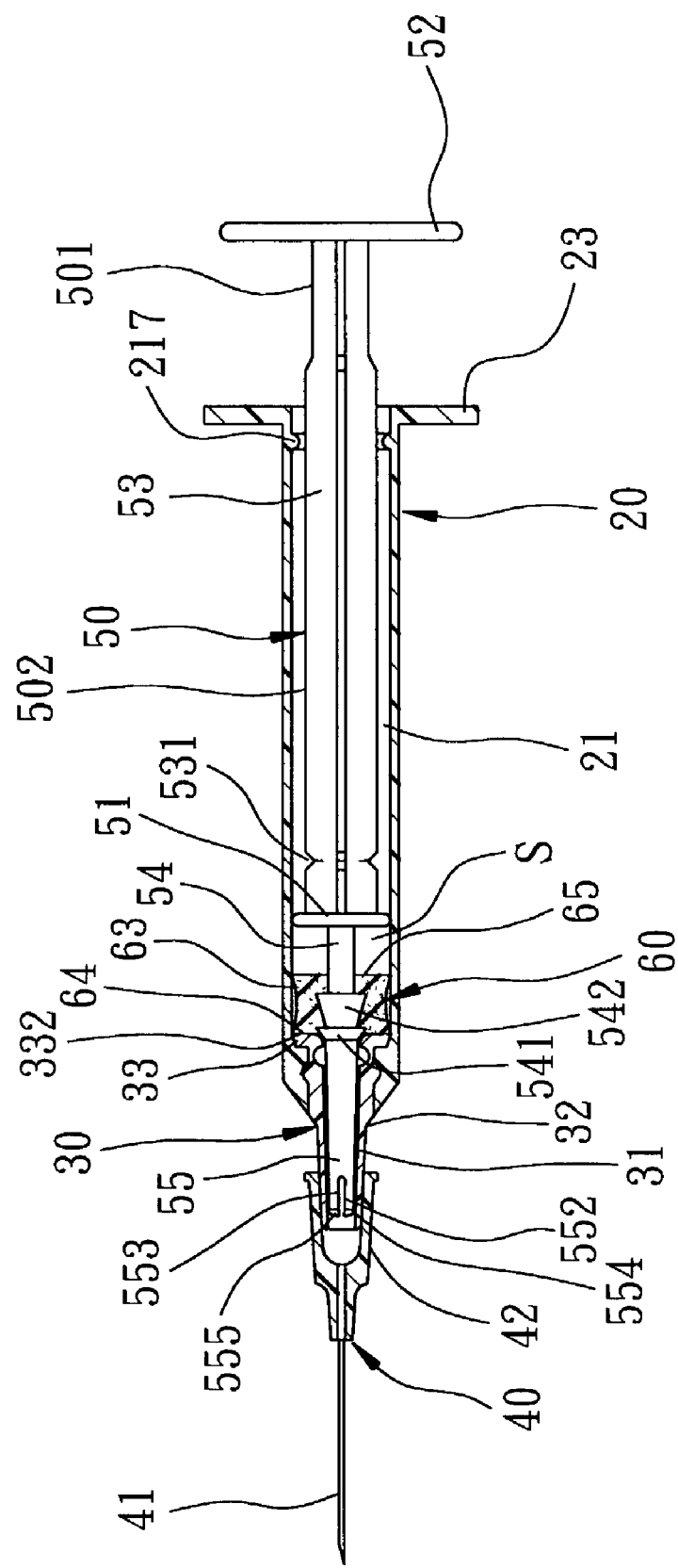
FIG. 5 is a longitudinal cross-sectional view showing the syringe assembly in a state of use.

With reference to FIG. 5, in use, the plunger 50 is pressed forwardly to push the upper end face 64 of the surrounding engaging portion 60 to abut against a lower edge surface 332 of the lower surrounding edge portion 33 of the needle seat 30. Since the spindle portion 55 is configured to be tapered upwardly and to match with the inner tubular wall surface 324 of the needle seat 30, drug solution in the passage 21 can almost be completely injected via the needle unit 40.

Figure 6:
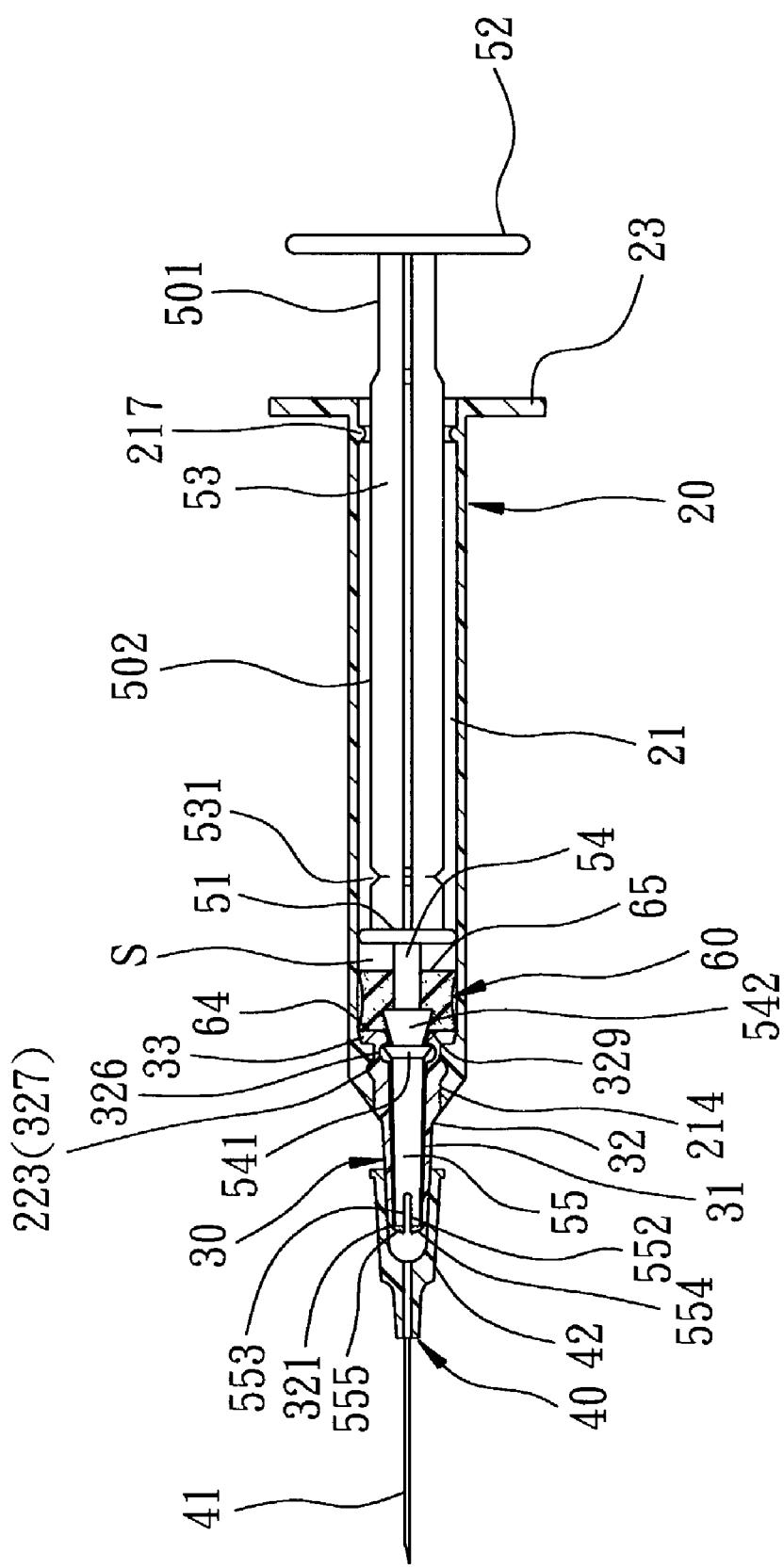
FIG. 6 is a longitudinal cross-sectional view showing the syringe assembly in a state in which a head of a plunger is held by a grip segment of a needle seat.

Subsequently, referring to FIG. 6, when the plunger 50 is further moved forward by a third force towards the smaller-diameter segment 214 against the second friction force between the inner segment 502 and the surrounding engaging portion 60, the surrounding engaging portion 60 is deformed by the lower surrounding edge portion 33, thereby decreasing the space (S) and permitting the surrounding abutting portion 541 of the head to move in the concave portion 326 of the needle seat 30 to abut against the second surrounding shoulder portion 329.

Meanwhile, the split halves 552, 553 of the spindle portion 55 are pressed by the inner tubular wall surface 324 to move towards each other against a biasing action when the split halves 552, 553 are moved towards the upper surrounding edge portion 321. Once the split halves 552, 553 are moved beyond the upper surrounding edge portion 321, the upper terminal anchoring edges 554, 555 will engage the upper surrounding edge portion 321 to generate a friction force that combines with the friction force between the surrounding abutting portion 541 and the second surrounding shoulder portion 329 to form a fourth friction force that is greater than the first friction force between the retaining protrusion 327 and the retaining groove 223.

Figure 7:
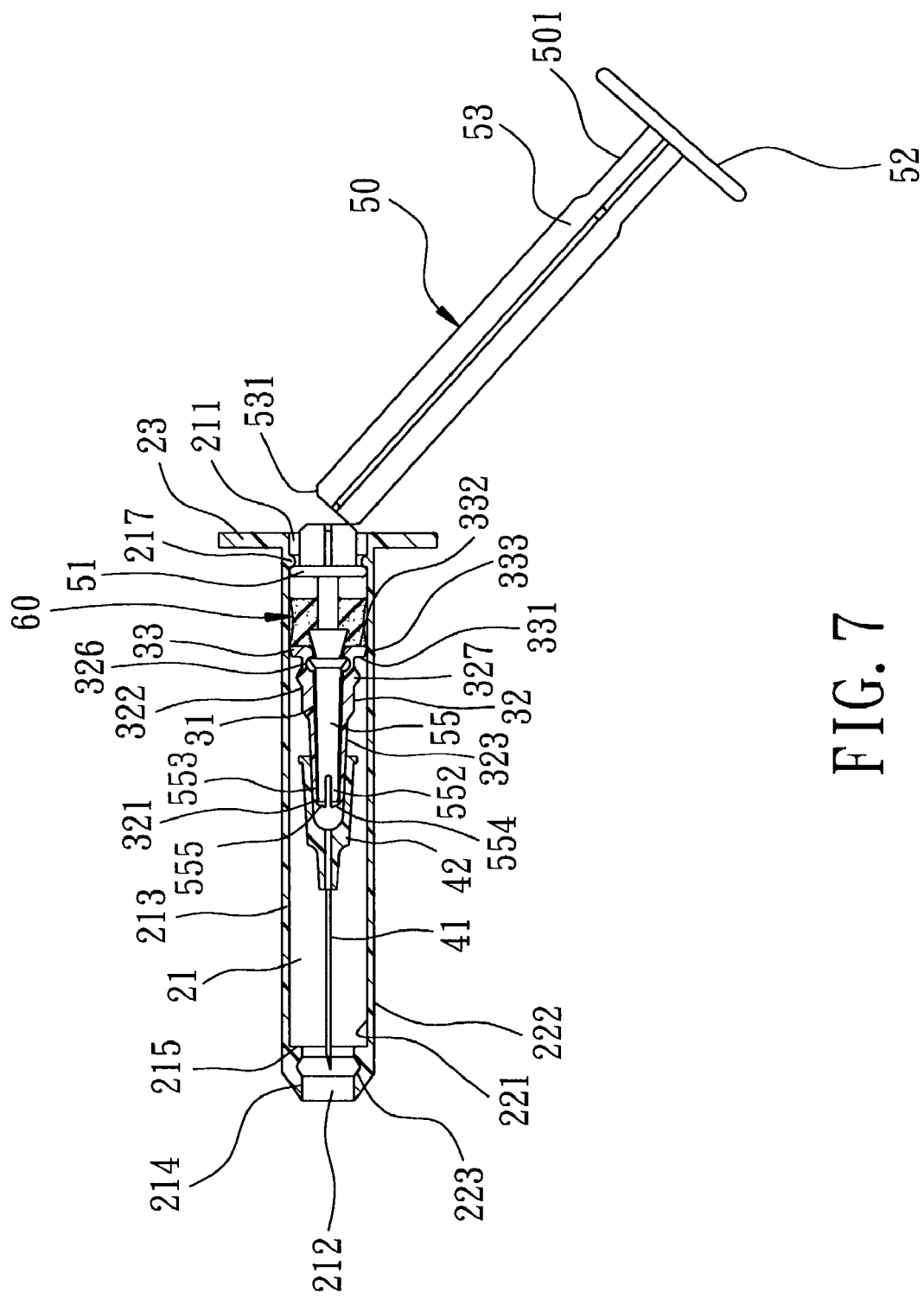
FIG. 7 is a longitudinal cross-sectional view showing the syringe assembly in a retracted state.

After use, referring to FIG. 7, the outer segment 501 of the plunger 50 is pulled backward to be remote from the finger flange 23 so that the needle seat 30, on which the used needle unit 40 is mounted, is retracted into the passage 21 via the upper open end 212 to bring the upper surrounding edge portion 321 to a retracted position. When the surrounding flange 51 abuts against the protruding ring 217, further movement of the plunger 50 is prevented, thereby restraining the surrounding engaging portion 60 from being removed out of the lower open end 211. In this state, the used needle unit 40 can be enclosed in the passage 21 of the barrel 20 for safe disposal.

Consequently, chances that the user may be accidentally pricked or pierced by the needle are slim. The safety in use and disposal is thus enhanced.

Furthermore, the wing plates 53 at the inner segment 502 have a weakening area 531 disposed proximate to the surrounding flange 51. As such, when the plunger 50 is retracted to push the surrounding flange 51 to abut against the protruding ring 217, the weakening area 531 extends outwardly of the lower open end 211 so as to ease breaking of the stem portion off the plunger 50 at the weakening area 531 for convenient disposal.

Figure 8:
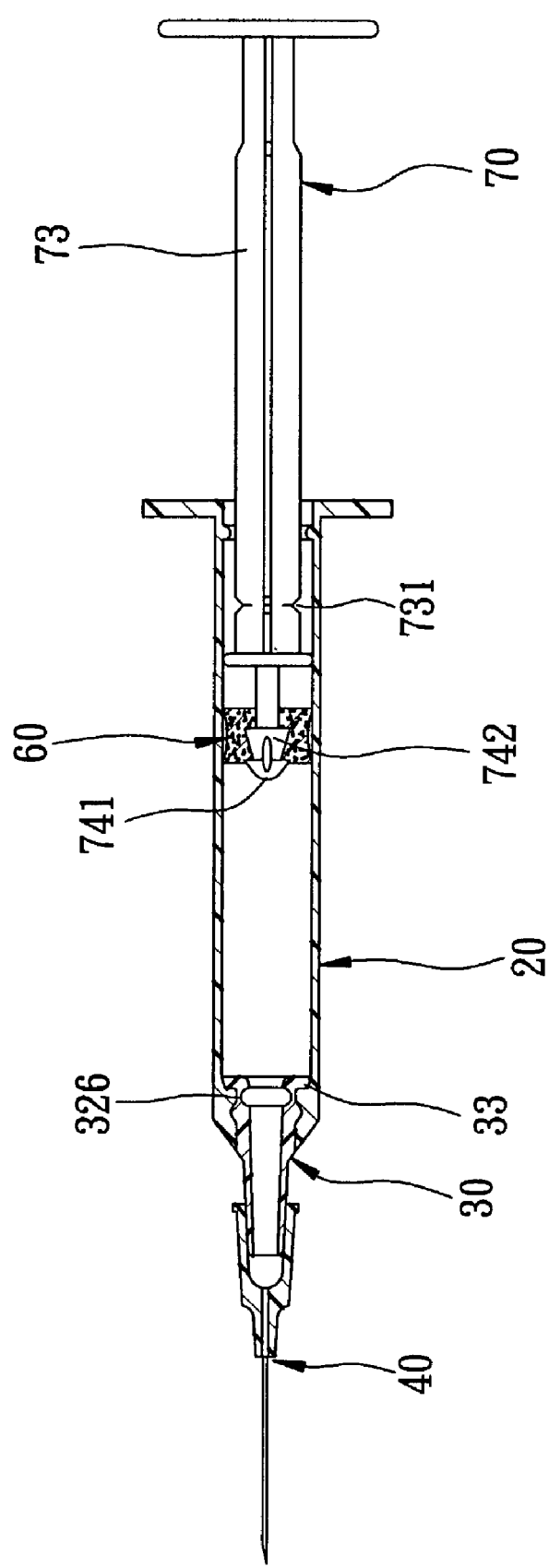
FIG. 8 is a longitudinal cross-sectional view showing a second preferred embodiment of a disposable syringe according to this invention for use with a needle unit to form a syringe assembly.
Figure 9:
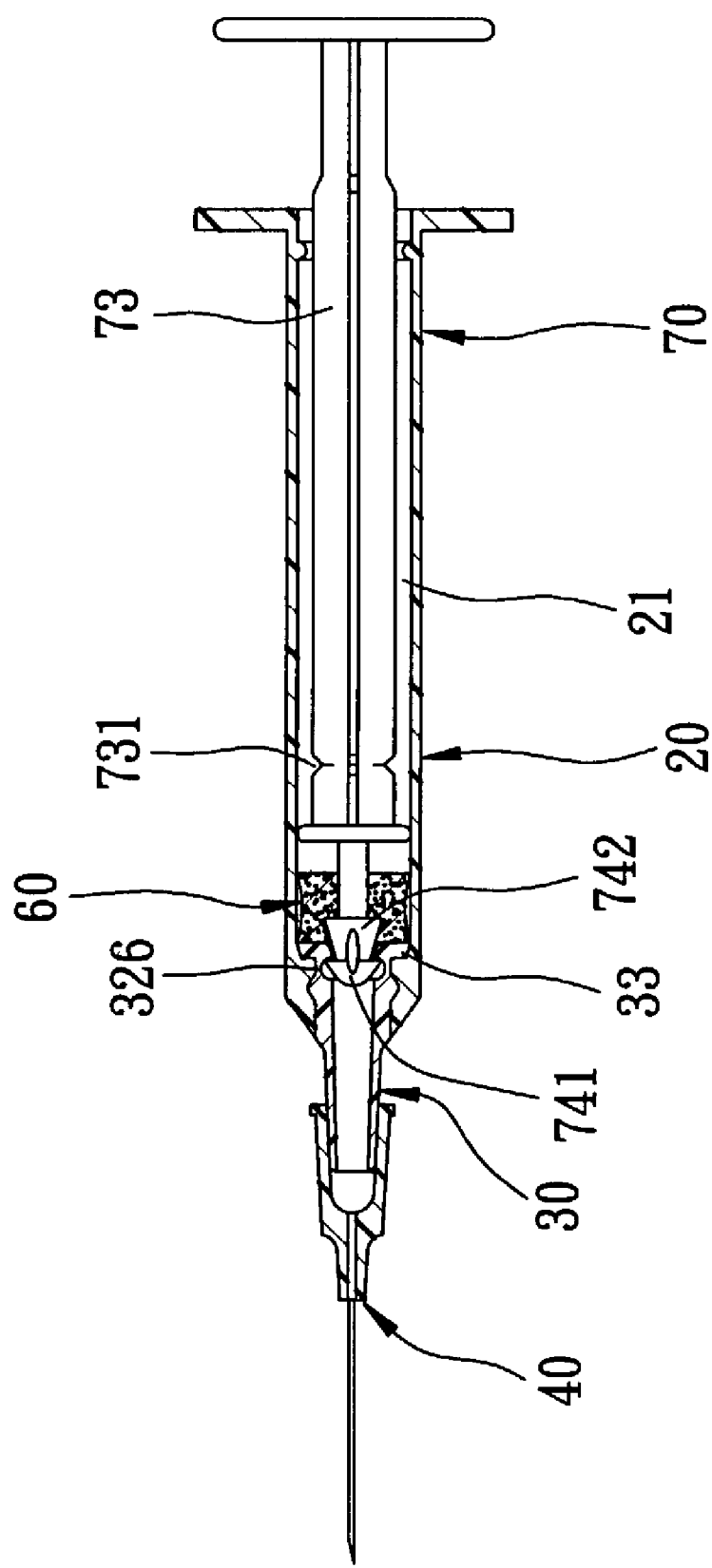
FIG. 9 is a longitudinal cross-sectional view showing the syringe assembly according to the second preferred embodiment in a state in which a head of a plunger is held by a grip segment of a needle seat.
Figure 10:
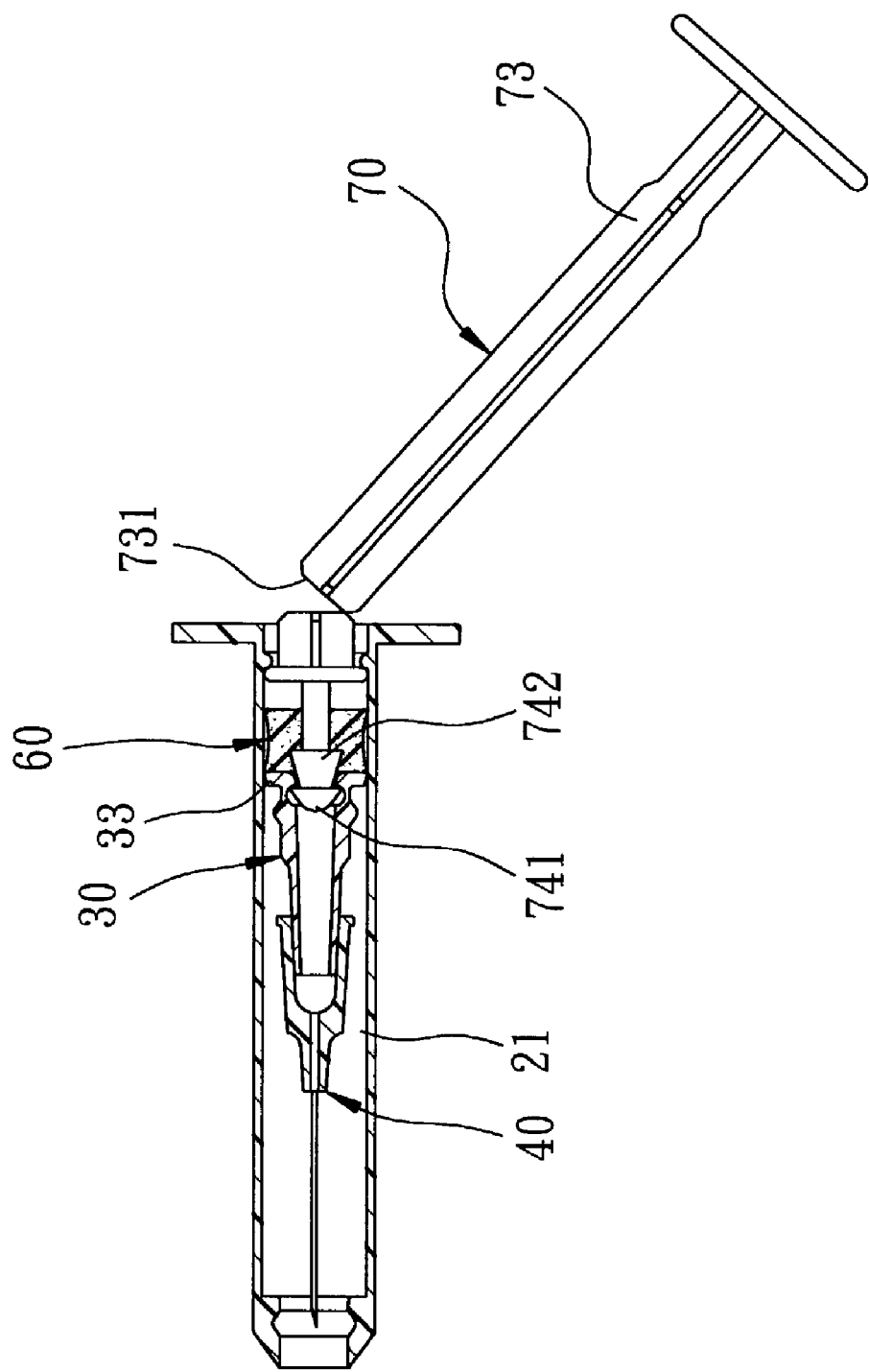
FIG. 10 is a longitudinal cross-sectional view showing the syringe assembly in a retracted state.

Referring to FIG. 8, the second preferred embodiment of the disposable syringe according to this invention is similar to the aforesaid embodiment in construction. The differences therebetween reside in that a retaining protrusion 742 and a surrounding abutting portion 741 of a plunger 70 are configured to be substantially hollow so as to provide a greater flexibility, and that the spindle portion in the aforesaid embodiment is dispensed with. An elastic surrounding engaging portion 60 is retainingly sleeved on the whole retaining protrusion 742 and a portion of the surrounding abutting portion 741. As such, when the surrounding engaging portion 60 is brought by the stem portion 73 of the plunger 70 upwardly to engage and is depressed by the lower surrounding edge portion 33 of the needle seat 30, the surrounding engaging portion 60 is blocked by the lower surrounding edge portion 33, thereby permitting the surrounding abutting portion 741 to be retained in the concave portion 326, as shown in FIG. 9. Hence, the needle seat 30 and the needle unit 40 can be retracted into the passage 21 of the barrel 20 after an injection procedure to permit breaking off the stem portion 73 of the plunger 70 at a weakening area 731 for safe disposal, as shown in FIG. 10.

While the present invention has been described in connection with what is considered the most practical and preferred embodiments, it is understood that this invention is not limited to the disclosed embodiments but is intended to cover various arrangements included within the spirit and scope of the broadest interpretations and equivalent arrangements.

We claim:

1. A disposable syringe adapted to be used with a needle unit which includes a needle hub and a needle securely affixed to the needle hub, said syringe comprising:

a barrel having an inner surrounding barrel wall surface which surrounds an axis and which confines a passage, said passage having lower and upper open ends which are disposed opposite to each other in a longitudinal direction parallel to the axis, said inner surrounding barrel wall surface including a larger-diameter segment and a smaller-diameter segment which are disposed proximate to said lower and upper open ends, respectively, and which cooperatively form a first surrounding shoulder portion therebetween, the smaller-diameter segment including a retaining groove defined therein;

a tubular needle seat disposed to be insertable into said passage from said lower open end toward said upper open end, said needle seat including a protruding lower surrounding edge portion which is disposed to abut against said first surrounding shoulder portion, an upper surrounding edge portion disposed opposite to said lower surrounding edge portion in the longitudinal direction, and a surrounding seat wall interposed between said lower and upper surrounding edge portions, and having an inner tubular wall surface which surrounds the axis to confine a duct and which has a grip segment, and an outer tubular wall surface which includes a lower segment including a retaining protrusion defined thereon and proximate to said lower surrounding edge portion, lower segment being configured such that, when said upper surrounding edge portion is forced to extend outwardly of said upper open end after said tubular needle seat is inserted into said passage, said lower segment will be brought to a position of use, where said lower segment engages and is retained at said smaller-diameter segment by virtue of a first friction force generated by retaining engagement of the retaining protrusion in the retaining groove while said protruding lower surrounding edge portion abuts against said first surrounding shoulder portion, the lower segment being further configured such that, when said upper surrounding edge portion is forced against the first friction force so as to be retracted into said passage via said upper open end, said upper surrounding edge portion will be brought to a retracted position, where said lower segment and said protruding lower surrounding edge portion are remote from said smaller-diameter segment and said first surrounding shoulder portion, respectively, and an upper segment disposed opposite to said lower segment and proximate to said upper surrounding edge portion, said upper segment being adapted to be sleeved over by the needle hub so as to communicate said duct with the needle hub; and a plunger including
  a stem portion which is disposed to be movable in said passage of said barrel and which has inner and outer segments opposite to each other in the longitudinal direction, said outer segment extending outwardly of said lower open end,
  an actuated end extending from said outer segment so as to be actuated to move said stem portion along said passage,
  a surrounding engaging portion which is disposed to be retainingly sleeved on said inner segment by virtue of a second friction force, and which in sealing contact with and which is slidable relative to said larger-diameter segment so as to be moved with said stem portion in the position of use, and
  a head disposed to extend from said inner segment toward said grip segment, and configured such that, when said surrounding engaging portion is brought by said inner segment to engage said lower surrounding edge portion and is depressed by said lower surrounding edge portion by virtue of a third force generated as a consequence of continuing movement of said inner segment towards said smaller-diameter segment, the third force being greater than the second friction force such that said surrounding engaging portion is blocked by said lower surrounding edge portion to thereby permit said head to move towards said grip segment of said tubular needle seat and to be held by virtue of a fourth friction force that is greater than the first friction force while said lower segment remains engaged and unmoved relative to said smaller-diameter segment.

2. The disposable syringe of claim 1, wherein one of said lower segment and said smaller-diameter segment is formed with a retaining groove, and the other one of said lower segment and said smaller-diameter segment is formed with a retaining protrusion which engages retainingly said retaining groove when said lower segment is in the position of use so as to generate the first friction force.

3. The disposable syringe of claim 1, wherein said grip segment has a concave portion which extends inwardly from said inner tubular wall surface in radial directions relative to the axis to form a second surrounding shoulder portion that is adjacent to said lower surrounding edge portion, said head having a surrounding abutting portion which is configured so as to be insertable into said concave portion and to abut against said second surrounding shoulder portion, thereby generating the fourth friction force to bring said upper surrounding edge portion to the retracted position.

4. The disposable syringe of claim 3, wherein said head further has a spindle portion which extends from said surrounding abutting portion along the axis and which terminates at two split halves that are spaced apart from each other in a direction transverse to the longitudinal direction, said split halves respectively having two upper terminal anchoring edges which are remote from said surrounding abutting portion and which are configured such that said split halves are pressed by said inner tubular wall surface to move towards each other against a biasing action when said split halves are moved towards said upper surrounding edge portion, and such that said upper terminal anchoring edges engage said upper surrounding edge portion once said split halves are moved beyond said upper surrounding edge portion.

5. The disposable syringe of claim 4, wherein said inner tubular wall surface has a diameter which gradually decreases from said lower surrounding edge portion to said upper surrounding edge portion, said spindle portion having an outer diameter which gradually decreases from said surrounding abutting portion to said split halves.

6. The disposable syringe of claim 3, wherein said surrounding abutting portion is configured to be substantially hollow so as to provide a greater flexibility.

7. The disposable syringe of claim 1, wherein said surrounding engaging portion is made of a deformable material, and has upper and lower end faces opposite to each other in the longitudinal direction and proximate to and distal from said lower surrounding edge portion, respectively, and an outer surrounding surface disposed between said upper and lower end faces and concaved toward the axis.

8. The disposable syringe of claim 1, wherein said lower surrounding edge portion has an upper edge surface which abuts against said first surrounding shoulder portion when said lower segment is in the position of use, and a lower edge surface for abutment and depression by said surrounding engaging portion.

9. The disposable syringe of claim 1, further comprising a spline member disposed between said smaller-diameter segment and said lower segment to prevent relative rotation therebetween.

10. The disposable syringe of claim 1, further comprising a protruding ring which is disposed on and which projects inwardly and radially from said larger-diameter segment adjacent to said lower open end, and a surrounding flange which is disposed to surround said inner segment adjacent to said head and which is engageable with said protruding ring.

11. The disposable syringe of claim 10, wherein said inner segment has a weakening area which is disposed proximate to said surrounding flange such that when said surrounding flange is brought to engage said protruding ring, said weakening area extends outwardly of said lower open end so as to ease breaking of said stem portion off said plunger at said weakening area.

* * * * *